United States Patent
Ihatsu (10) Patent No.: US 11,723,686 B2
(45) Date of Patent: Aug. 15, 2023

(54) TRANSPERINEAL STEPPER INCLUDING ROTATABLE TRANSDUCER PROBE AND SHAFT WITH INTERNAL CABLE

(71) Applicant: KONINKLIJKE PHILIPS N.V., Eindhoven (NL)

(72) Inventor: Mika Tapani Ihatsu, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 453 days.

(21) Appl. No.: 16/609,793

(22) PCT Filed: Apr. 24, 2018

(86) PCT No.: PCT/EP2018/060413
§ 371 (c)(1),
(2) Date: Oct. 31, 2019

(87) PCT Pub. No.: WO2018/202470
PCT Pub. Date: Nov. 8, 2018

(65) Prior Publication Data
US 2020/0054357 A1    Feb. 20, 2020

Related U.S. Application Data
(60) Provisional application No. 62/500,122, filed on May 2, 2017.

(51) Int. Cl.
*A61B 17/00* (2006.01)
*A61B 8/00* (2006.01)
(Continued)

(52) U.S. Cl.
CPC ........ *A61B 17/3403* (2013.01); *A61B 8/4461* (2013.01); *A61B 10/0233* (2013.01);
(Continued)

(58) Field of Classification Search
CPC .............. A61B 17/3403; A61B 8/4461; A61B 10/0233; A61B 2017/3411;
(Continued)

(56) References Cited

U.S. PATENT DOCUMENTS 6,036,649 A    3/2000   Yuasa
6,325,760 B1   12/2001  Takanori et al.
(Continued)

FOREIGN PATENT DOCUMENTS

| | | | |
|---|---|---|---|
| JP | 2006320590 A | * | 11/2006 |
| JP | 2006320590 A | | 11/2006 |
| JP | 2015023996 A | | 2/2015 |

OTHER PUBLICATIONS

Search Report and Written Opinion from PCT/EP2018/060413 dated Jun. 28, 2018.

*Primary Examiner* — Amelie R Davis
*Assistant Examiner* — Neshat Baset
(74) *Attorney, Agent, or Firm* — Sherry Austin (57) ABSTRACT

A device includes an ultrasound probe including an elongated neck insertable in a patient and rotatable around a first longitudinal axis, an ultrasound transducer, and an elongated body rotatable around a second longitudinal axis that is parallel to and offset from the first longitudinal axis. The elongated body is removably attached to a probe mounting structure. A shaft is attached to the probe mounting structure, where rotation of the shaft causes corresponding rotation of the probe mounting structure and the attached elongated body of the ultrasound probe. The shaft defines a longitudinal shaft channel in an interior portion and a longitudinal shaft groove extending from a surface of the shaft to the longitudinal shaft channel. A cable is insertable into the longitudinal shaft channel through the longitudinal shaft groove, and enters an internal channel of the ultrasound (Continued)

probe through the longitudinal shaft channel enabling electrical connection with the ultrasound transducer.

9 Claims, 8 Drawing Sheets

(51) Int. Cl.
*A61B 10/02* (2006.01)
*A61B 17/34* (2006.01)

(52) U.S. Cl.
CPC ............... *A61B 2017/3411* (2013.01); *A61B 2017/3413* (2013.01)

(58) Field of Classification Search
CPC ............ A61B 2017/3413; A61B 8/445; A61B 10/0241; A61B 2017/00274; A61B 2034/2063; A61B 8/4209; A61B 8/0841; A61B 8/085; A61B 8/12; A61N 5/1001
See application file for complete search history.

(56) References Cited

U.S. PATENT DOCUMENTS

| | | |
|---|---|---|
| 8,758,256 B2 | 6/2014 | O'Laughlin |
| 2004/0143188 A1 | 7/2004 | Barzell et al. |
| 2007/0129634 A1 | 6/2007 | Hickey et al. |
| 2008/0249403 A1 | 10/2008 | Suri et al. |
| 2009/0227874 A1 | 9/2009 | Suri et al. |
| 2015/0366544 A1 | 12/2015 | Yap et al. |
| 2016/0338675 A1* | 11/2016 | Kubota ............... A61B 17/3403 |
| 2017/0020558 A1* | 1/2017 | Xu ......................... A61B 8/483 |

* cited by examiner

TRANSPERINEAL STEPPER INCLUDING ROTATABLE TRANSDUCER PROBE AND SHAFT WITH INTERNAL CABLE

CROSS REFERENCE TO RELATED APPLICATIONS

This application is a U.S. national phase application of International Application No. PCT/EP2018/060413 filed on Apr. 24, 2018, which claims the benefit of U.S. Provisional Application Ser. No. 62/500,122 filed May 2, 2017 and is incorporated herein by reference.

BACKGROUND

A transperineal stepper is configured to drive a biopsy needle through an intended location of the perineum (i.e., the area between the anus and the scrotum or vulva of a patient). A grid plate having a pattern or array of grid holes is positioned at a distal end of the transperineal stepper in order to provide guidance for one or more biopsy needles. The transperineal stepper includes an ultrasound probe insertable into the rectum of the patient, a cradle configured to rotate the ultrasound probe to various angles during a procedure, and a base configured to move the ultrasound probe longitudinally. The grid plate is attachable to the transperineal stepper, and different kinds of grid plates may be used, which vary in pattern and hole size, for example. The grid plate may be a reusable or disposal part. The ultrasound probe provides ultrasound images from within the patient's body, as well as stabilizes the positioning of the transperineal stepper.

Figure 1A:
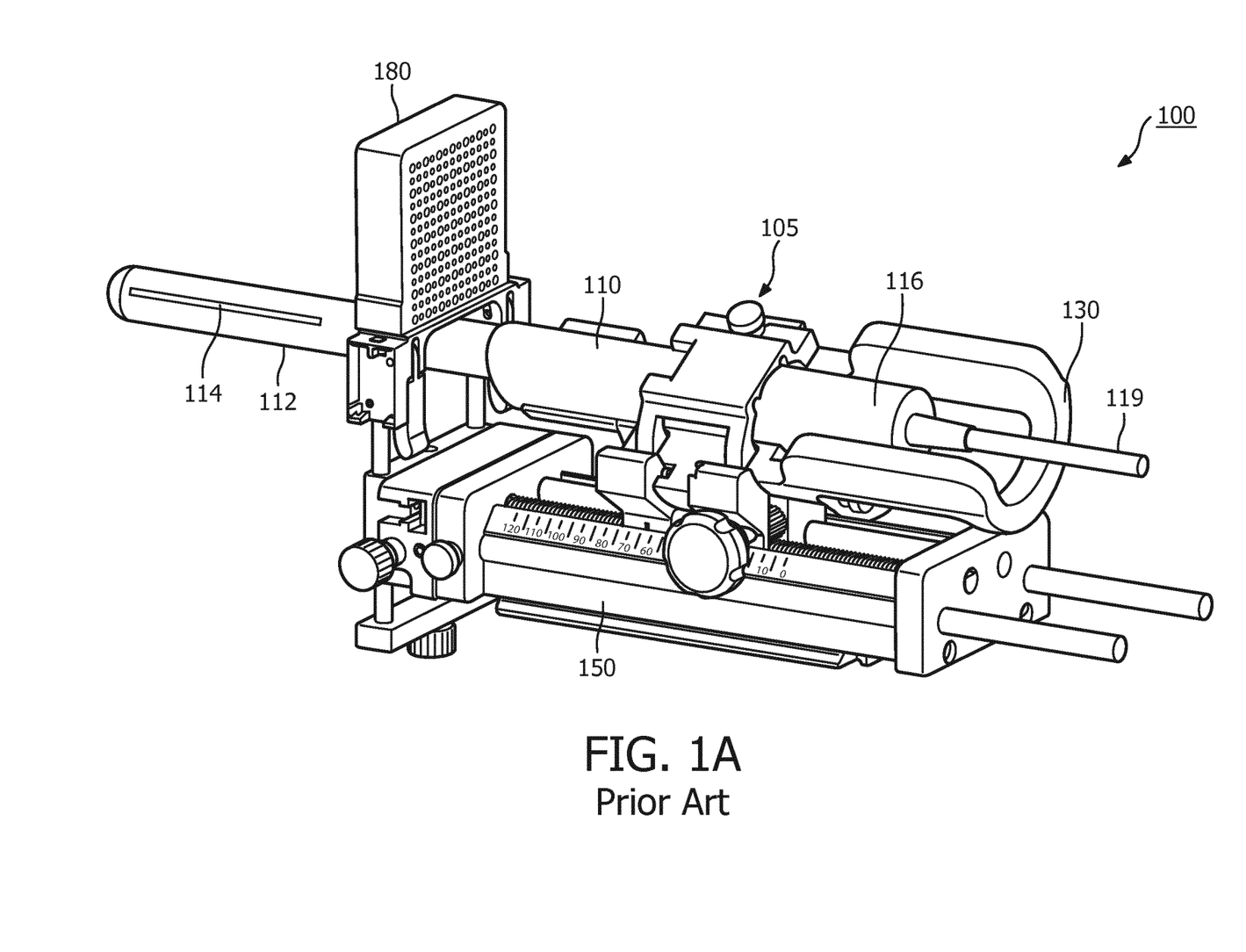
FIG. 1A is a perspective view of a conventional system including a transperineal stepper with a cradle and attached grid plate.
Figure 1B:
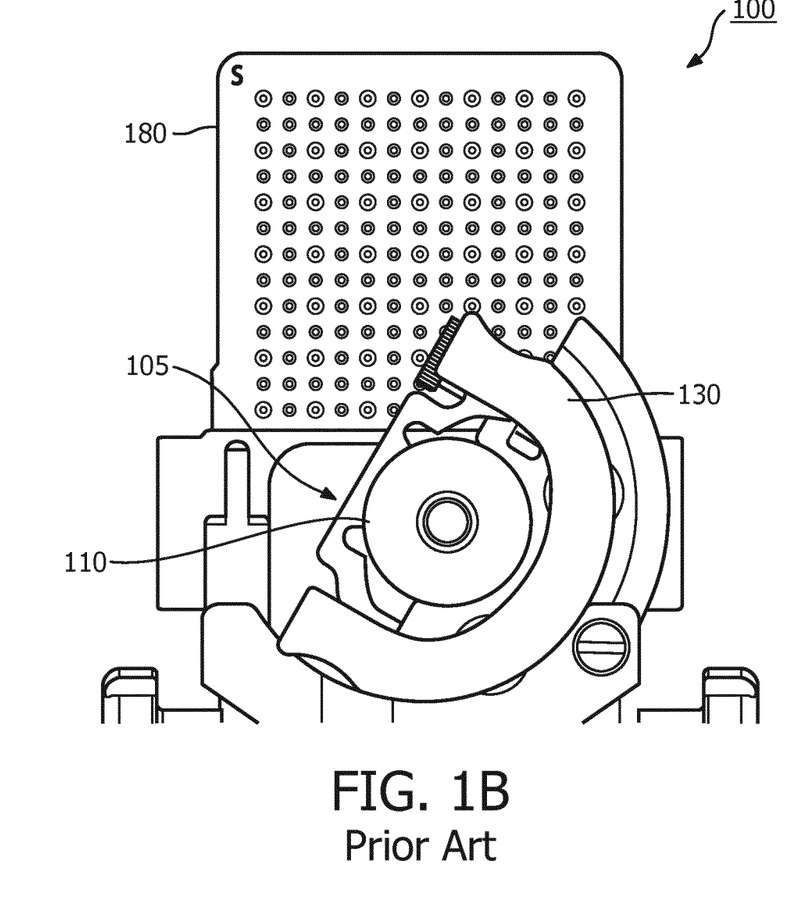
FIG. 1B is a back view of the conventional system in FIG. 1A including a transperineal stepper with a cradle and attached grid plate.

FIG. 1A is a perspective view of a conventional transperineal stepper system 100, including a transperineal stepper 105, having an ultrasound probe 110 positioned in a conventional cradle 130, a base 150, and a grid plate 180. FIG. 1B is a back plane view of the conventional transperineal stepper system 100 (as viewed from the proximal end of the transperineal stepper 105). The ultrasound probe 110 includes an elongated neck 112, at least one ultrasound transducer 114 connected to a distal end of the elongated neck 112, and an elongated body 116 connected to a proximal end of the elongated neck 112. The grid plate 180 is shown to include an array of grid holes, e.g., which are needle guides through which a needle can be placed. Although in FIGS. 1A and 1B, the grid plate 180 may appear to be a simple device, the grid plate 180 can be used in conjunction with other medical equipment for medical procedures that require extraordinarily precise control of, for example, biopsy needles. For example, as mentioned above, the transperineal stepper 105 may be used with the grid plate 180 to drive a biopsy needle through an intended location of the perineum. The ultrasound probe 110 is configured to move longitudinally beneath the grid plate 180, for insertion in the rectum of the patient, and to rotate through operation of the cradle 130 for obtaining images at different angles from within the patient's body.

The rotation is achieved by rotating the ultrasound probe 110 around a center of rotation (first longitudinal axis) of the elongated neck 112, which is different from a center of rotation (second longitudinal axis) of the elongated body 116. That is, the first longitudinal axis is offset from the second longitudinal axis, making the design of the cradle 130 problematic. For example, the cradle 130 may reach a rotation window of about 90 degrees to about 160 degrees, but it is not very stable on the edges of the rotation. Also, because a minimum diameter of the cradle 130 is heavily dependent on the geometry of the ultrasound probe 110, the minimum diameter is usually relatively large. The relatively large diameter blocks access to the grid plate 180 when the cradle is rotated, particularly to the edges of the rotation, as shown in FIG. 1B, for example, preventing insertion of biopsy needles through the blocked holes.

Furthermore, the design of the cradle 130 is fairly complicated. To work properly, the cradle 130 requires tight tolerances in certain features where it is difficult to maintain manufacturing accuracy. Therefore, the cradle 130 usually needs fine tuning screws and other adjusters, which are problematic to produce, and render each cradle 130 and thus each transperineal stepper 105 unique. Also, the smooth rotation of the cradle 130 is very sensitive for a moment which generates when the elongated neck 112 is pushed in use. The design of the cradle 130 makes it fairly difficult to design a rotation handle which would generate a smooth and accurate rotation. Also, as a practical matter, the cradle 130 is difficult to clean and keep clean.

It is possible to replace the cradle design by a shaft design (not shown), which includes placement of a rotational shaft that engages at the proximal end of the ultrasound probe 110 to provide rotation. However, cable management becomes problematic using the shaft design since cable 119, for providing power and electrical signals to the ultrasound transducer 114, is attached to the proximal end of the ultrasound probe, interfering with rotational movement of the shaft.

Therefore, a transperineal stepper is needed that has efficient and easily operated means for rotating the ultrasound probe, without interfering with other aspects of transperineal stepper operation, such as effective cable management or increased size.

SUMMARY

According to an aspect of the present disclosure, a device is provided that includes an ultrasound probe, a shaft and at least one cable. The ultrasound probe includes an elongated neck insertable in a patient and rotatable around a first longitudinal axis, where at least one ultrasound transducer is connected to a distal end of the elongated neck, and an elongated body connected to a proximal end of the elongated neck and rotatable around a second longitudinal axis that is parallel to and offset from the first longitudinal axis, where the elongated body is removably attached to a probe mounting structure. The shaft is arranged at a proximal end of the elongated body and attached to a proximal end of the probe mounting structure. Rotation of the shaft causes corresponding rotation of the probe mounting structure and the attached elongated body of the ultrasound probe around the second longitudinal axis to a desired position, where the shaft defines a longitudinal shaft channel in an interior portion of the shaft and a longitudinal shaft groove extending from a surface of the shaft to the longitudinal shaft channel. The at least one cable provides electrical connections to the at least one ultrasound transducer, where the at least one cable is insertable into the longitudinal shaft channel through the longitudinal shaft groove, and enters an internal channel of the ultrasound probe through the longitudinal shaft channel to enable electrical connection with the at least one ultrasound transducer.

The at least one ultrasound transducer may include an ultrasound transducer array.

The shaft is a rotatable around a third longitudinal axis that is parallel to and longitudinally aligned with the first longitudinal axis of the elongated neck. The device further includes a shaft housing containing the shaft, the shaft being rotatable around the third longitudinal axis within the shaft housing. The shaft housing defines a longitudinal housing groove that is alignable with the longitudinal shaft groove in the shaft to enable placement of the at least one cable within the longitudinal shaft groove. The device further includes a handle containing the shaft housing and connected to the shaft within the shaft housing, preventing the shaft from sliding, where rotation of the handle causes corresponding rotation of the shaft around the third longitudinal axis of the shaft. The handle defines a longitudinal handle groove alignable with the longitudinal housing groove and aligned with the longitudinal shaft groove, enabling placement of the at least one cable in the longitudinal shaft groove.

The probe mounting structure may include a support configured to receive the elongated body of the ultrasound probe, and a clamp configured to mechanically secure the elongated body in the support, such that the elongated body is in a fixed position relative to the probe mounting structure. The probe mounting structure may further include a flange at the proximal end of the probe mounting structure, where the shaft is attached to the flange. The device may further include a base connected between the shaft housing and a grid plate having an array of grid holes, where at least one needle is guided through at least one hole of the array of grid holes. The base may include a longitudinal translation device arranged between the shaft housing and the grid plate, enabling movement, as a unit, of the shaft housing, the shaft contained in the shaft housing, the probe mounting structure attached to the shaft, and the elongated body of the ultrasound probe secured to the probe mounting structure toward and away from the grid plate. The longitudinal translation device may include at least one longitudinal bore in the base, and at least one rod attached to the shaft housing at a proximal end of the at least one rod, and configured to move longitudinally through the at least one longitudinal bore in the base.

According to another aspect of the present disclosure, a transperineal stepper is provided that includes an ultrasound probe, a probe mounting structure and a shaft. The ultrasound probe includes at least one ultrasound transducer connected to a distal end of the ultrasound probe, and a cable attached to a proximal end of the ultrasound probe for providing electrical connection to the at least one ultrasound transducer. The ultrasound probe is attached to the probe mounting structure. The shaft is connected to a proximal end of the probe mounting structure, the shaft defining a longitudinal shaft channel in an interior portion of the shaft and a longitudinal shaft groove extending from a surface of the shaft to the longitudinal shaft channel, enabling placement of the cable in the longitudinal shaft channel. Rotation of the shaft causes corresponding rotation of the probe mounting structure and the ultrasound probe attached to the probe mounting structure, while the cable remains in the longitudinal shaft channel, to position the at least one ultrasound transducer at a desired angle.

The ultrasound probe of the transperineal stepper may further include an elongated neck rotatable around a first longitudinal axis, the at least one ultrasound transducer being connected to a distal end of the elongated neck, and an elongated body connected to a proximal end of the elongated neck and rotatable around a second longitudinal axis that is parallel to and offset from the first longitudinal axis. The rotation of the shaft may cause corresponding rotation of the probe mounting structure and the elongated body of the ultrasound probe around the second longitudinal axis, and the rotation of the elongated body may cause corresponding rotation of the elongated neck around the first longitudinal axis to position the at least one ultrasound transducer at the desired angle. The shaft may be rotatable around a third longitudinal axis that is parallel to and longitudinally aligned with the first longitudinal axis of the elongated neck.

The transperineal stepper may further include a shaft housing containing the shaft, the shaft being rotatable around the third longitudinal axis within the shaft housing, where the shaft housing defines a longitudinal housing groove that is alignable with the longitudinal shaft groove in the shaft to enable placement of the cable within the longitudinal shaft groove. The transperineal stepper may further include a handle containing the shaft housing and connected to the shaft, rotation of the handle causing corresponding rotation of the shaft around the third longitudinal axis within the shaft housing. The handle may define a longitudinal handle groove alignable with the longitudinal housing groove and aligned with the longitudinal shaft groove, enabling placement of the at least one cable in the longitudinal shaft groove. The handle groove may remain aligned with the longitudinal shaft groove during rotation of the shaft within the shaft housing around the third longitudinal axis.

The transperineal stepper may further include a base, and a longitudinal translation device including at least one longitudinal bore in the base, and at least one rod attached to the shaft housing at a proximal end of the at least one rod, and configured to move longitudinally through the at least one longitudinal bore in the base, enabling longitudinal movement, as a unit, of the shaft housing, the shaft contained in the shaft housing, the probe mounting structure attached to the shaft, and the ultrasound probe secured to the probe mounting structure. A grid plate may be connected to a distal end of the base, the grid plate having an array of grid holes, where at least one needle may be guided through at least one hole of the array of grid holes during operation of the at least one ultrasound transducer.

According to yet another aspect of the present disclosure, a device is provided that includes an ultrasound probe, a probe mounting structure, a shaft, a shaft housing and a handle. The ultrasound probe includes at least one ultrasound transducer connected to a distal end of the ultrasound probe, and a cable attached to a proximal end of the ultrasound probe for providing electrical connection to the at least one ultrasound transducer. The probe mounting structure is provided, where the ultrasound probe is removably attached to the probe mounting structure. The shaft is connected to a proximal end of the probe mounting structure, where the shaft defines a longitudinal shaft channel in an interior portion of the shaft and a longitudinal shaft groove extending from a surface of the shaft to the longitudinal shaft channel. The shaft housing is provided, such that the shaft is rotatable within the shaft housing, and where the shaft housing defines a longitudinal housing groove that is alignable with the longitudinal shaft groove in the shaft. The handle is connected to the shaft, where the handle defines a longitudinal handle groove that is in a fixed alignment with the longitudinal shaft groove and alignable with the longitudinal housing groove in a neutral position of the shaft, to enable placement of the cable within the longitudinal shaft groove. Rotation of the handle causes corresponding rotation of the shaft within the shaft housing, and the rotation of the shaft causes corresponding rotation of the probe mounting structure and the ultrasound probe attached to the probe mounting structure, while the cable remains in the longitudinal shaft channel.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms "a", "an" and "the" are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Figures 2, 3A:
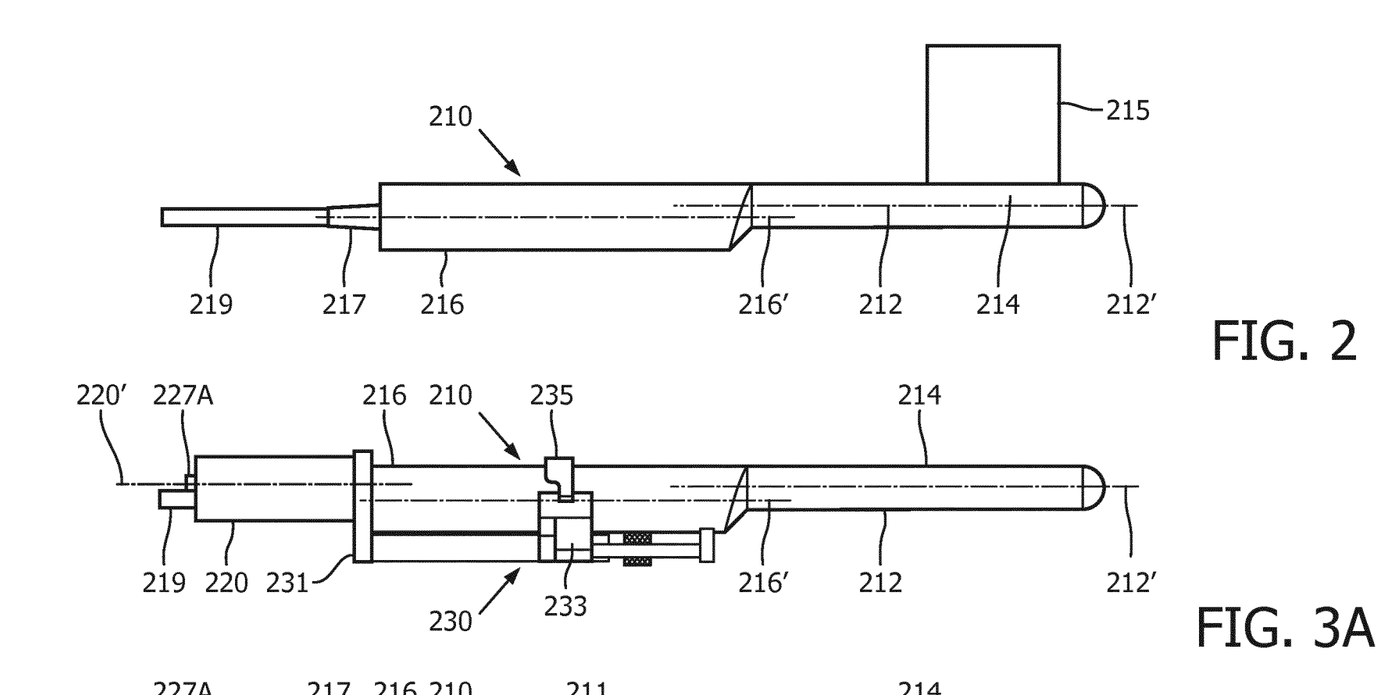
FIG. 2 is a side view of an ultrasound probe for use in a transperineal stepper, according to a representative embodiment.
FIG. 3A is a side view of the ultrasound probe and a probe mounting structure attached to a rotating shaft for use in a transperineal stepper, according to a representative embodiment.

FIG. 2 is a side view of an ultrasound probe for use in a transperineal stepper, according to a representative embodiment.

Referring to FIG. 2, an ultrasound probe 210 includes an elongated neck 212, at least one ultrasound transducer 214 connected to a distal end of the elongated neck 212, and an elongated body 216 connected to a proximal end of the elongated neck 212. The elongated neck 212 is insertable in a patient and rotatable around a first longitudinal axis 212', which corresponds to a center longitudinal axis of the elongated neck 212. For example, the elongated neck 212 may be configured to be inserted into the rectum of the patient, and rotated to various angles around the first longitudinal axis 212' to provide images with different views from the ultrasound transducer 214. In the depicted embodiment, the ultrasound transducer 214 is an ultrasound transducer array, comprising multiple ultrasound transducers typically arranged in a row and column configuration, providing illustrative image field 215. Of course, the ultrasound transducer 214 may be implemented as various numbers, types and/or arrangements without departing from the scope of the present teachings. The elongated body 216 is rotatable around a second longitudinal axis 216', which corresponds to a center longitudinal axis of the elongated body 216. The second longitudinal axis 216' is parallel to and laterally offset from the first longitudinal axis 212'.

The ultrasound probe 210 also includes a strain relief 217 and a cable 219 inserted through the strain relief 217. The strain relief 217 protects a mount point of the cable 219 from stresses induced by maneuvering, such as pulling, pushing and rotating the ultrasound probe 210. The cable 219 runs through the strain relief 217 to access an internal channel (e.g., internal channel 211 shown in FIG. 3B) of the ultrasound probe 210, to provide electrical connections with the (at least one) ultrasound transducer 214. In the depicted example, the cable 219 runs the length of the ultrasound probe 210 within the internal channel 211 to the ultrasound transducer 214. In alternative configurations, the cable 219 ends short of the ultrasound probe 210, connecting to a combiner board (not shown) inside the ultrasound transducer 214, which provides separate internal wiring.

Figure 3B:
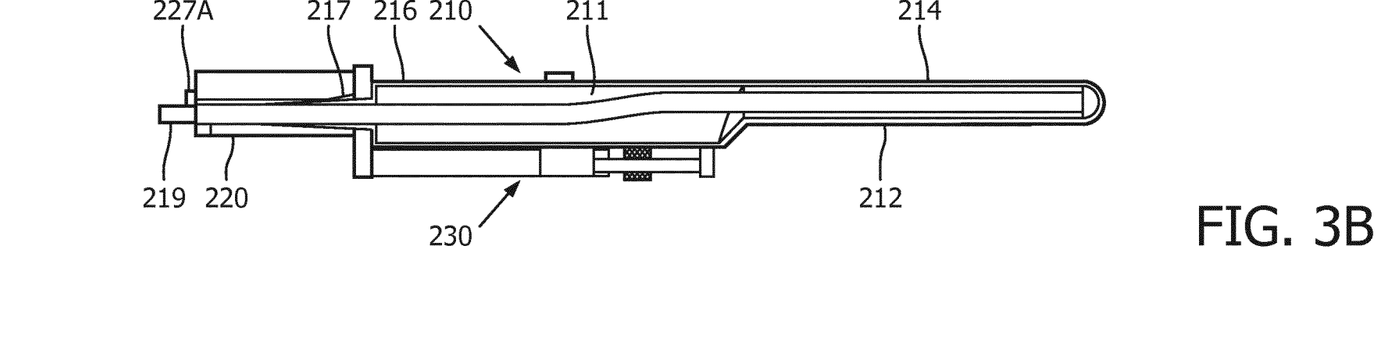
FIG. 3B is a cross-sectional view of the ultrasound probe and a probe mounting structure attached to the rotating shaft for use in the transperineal stepper, according to a representative embodiment.
Figure 4:
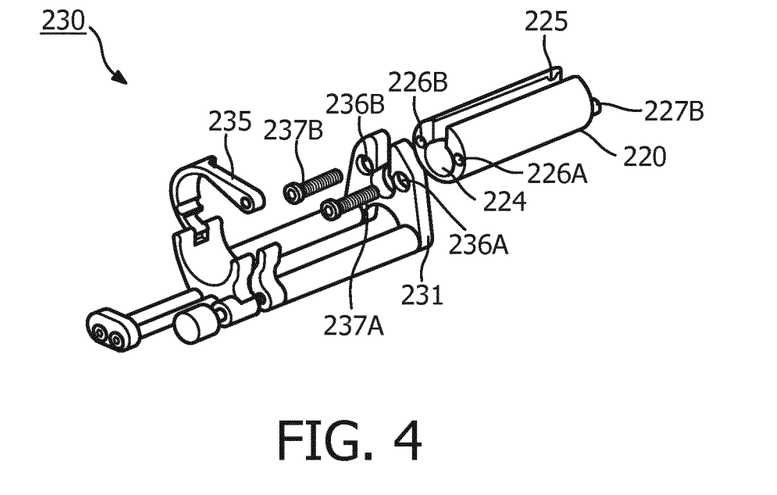
FIG. 4 is an exploded perspective view of the probe mounting structure and the rotating shaft of FIGS. 3A and 3B for use in a transperineal stepper, according to a representative embodiment.

FIG. 3A is a side view and FIG. 3B is a cross-sectional view of an ultrasound probe and a probe mounting structure attached to a rotating shaft for use in a transperineal stepper, according to a representative embodiment. FIG. 4 is an exploded perspective view of an illustrative probe mounting structure and a rotating shaft for use in a transperineal stepper, according to a representative embodiment.

Referring to FIGS. 3A, 3B and 4, the ultrasound probe 210 is attached to a probe mounting structure 230, which is attached to a shaft 220. Thus, the shaft 220 is arranged at the proximal end of the elongated body 216 of the ultrasound probe 210. The probe mounting structure 230 includes a support 233 configured to receive the elongated body 216 of the ultrasound probe 210, and a clamp 235 configured to mechanically secure the elongated body 216 in the support 233, such that the elongated body 216 is held in a fixed position relative to the probe mounting structure 230. In the depicted example, each of the support 233 and the clamp 235 has a concave shape to receive the substantially tubular shaped ultrasound probe 210. Of course, the support 233 and the clamp 235 may have alternative shapes to accommodate the particular shape of the type of ultrasound probe that it connects to the probe mounting structure 230, without departing from the scope of the present teachings. Likewise, connection means other than the paired support 233 and clamp 235 may be incorporated, without departing from the scope of the present teachings.

Referring again to the depicted example, the probe mounting structure 230 further includes a flange 231 at its proximal end. The flange 231 defines holes 236A and 236B that align with holes 226A and 226B in the distal end of the shaft 220. The aligned holes 236A/226A and 236B/226B respectively receive screws 237A and 237B to mechanically secure or attach the shaft 220 to the flange 231. Any other means of securely attaching the shaft 220 to the flange 231, such as bolts, rivets, clamps or solder, for example, may be incorporated without departing from the scope of the present teachings, as would be apparent to one skilled in the art. The shaft 220 also includes a set of pins, pins 227A and 227B, protruding from the proximal end of the shaft 220. The pins 227A and 227B are used to attach the shaft 220 to a handle (e.g., rotating handle 260 shown in FIGS. 8A and 8B) used to rotate the shaft 220, as discussed below.

The shaft 220 is rotatable around a third longitudinal axis 220', which corresponds to a center longitudinal axis of the shaft 220. In the depicted embodiment, the third longitudinal axis 220' is parallel to and aligned with the first longitudinal axis 212' of the elongated neck 212. Rotation of the shaft 220 causes corresponding rotation of the probe mounting structure 230 and the attached elongated body 216 of the ultrasound probe 210 around the second longitudinal axis 216' to a desired position. Rotation of the elongated body 216 translates into rotation of the elongated neck 212 around the first longitudinal axis 212', placing the ultrasound transducer 214 at a desired angle for ultrasound imaging.

Figure 5:
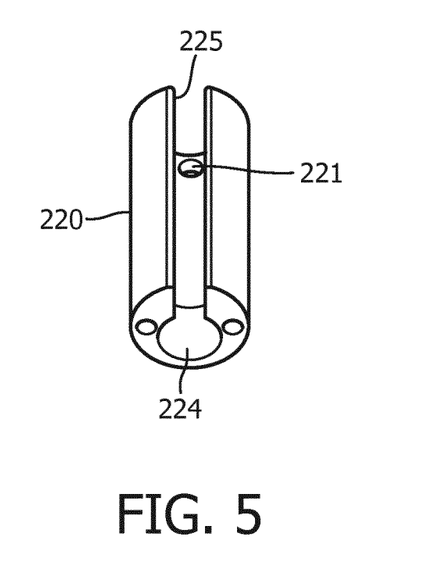
FIG. 5 is a perspective view of the rotating shaft for use in the transperineal stepper, according to a representative embodiment.

FIG. 5 is a perspective view of the rotating shaft of FIGS. 3A and 3B for use in the transperineal stepper, according to a representative embodiment.

Referring to FIGS. 4 and 5, the shaft 220 defines a longitudinal shaft channel 224 and a longitudinal shaft groove 225. The shaft channel 224 passes through an interior portion of the shaft 220 along the length of the shaft 220 (between proximal and distal ends). The shaft groove 225 parallels the shaft channel 224 along the length of the shaft 220 in the longitudinal direction, and also extends inwardly from an outer surface of the shaft 220 to the shaft channel 224, enabling open access to the shaft channel 224. Thus, the cable 219, for example, is insertable into the shaft channel 224 (and subsequently into the internal channel 211 of the ultrasound probe 210, as discussed above) by passing through the shaft groove 225 in the shaft 220. The shaft 220 also includes a hole 221 at the bottom of the shaft channel 224 to enable physical attachment to an operational handle (e.g., handle 260), discussed below.

Accordingly, beginning at the proximal end of the shaft 220, none of the cable 219 runs externally, preventing the cable 219 from interfering with movement of the ultrasound probe 210 and/or its supporting structure. That is, running the cable 219 internally through the shaft channel 224 improves cable management while manipulating the ultrasound probe 210 during medical procedures. Notably, although a single cable 219 is shown for purposes of illustration, it is understood that the cable 219 may be representative of multiple (two or more) cables passing through the internal channel 211 of the shaft 220 and providing wired connections to the ultrasound transducer 214. The cable 219 may provide electrical power to and/or exchange electrical signaling with the ultrasound transducer 214.

Figure 6:
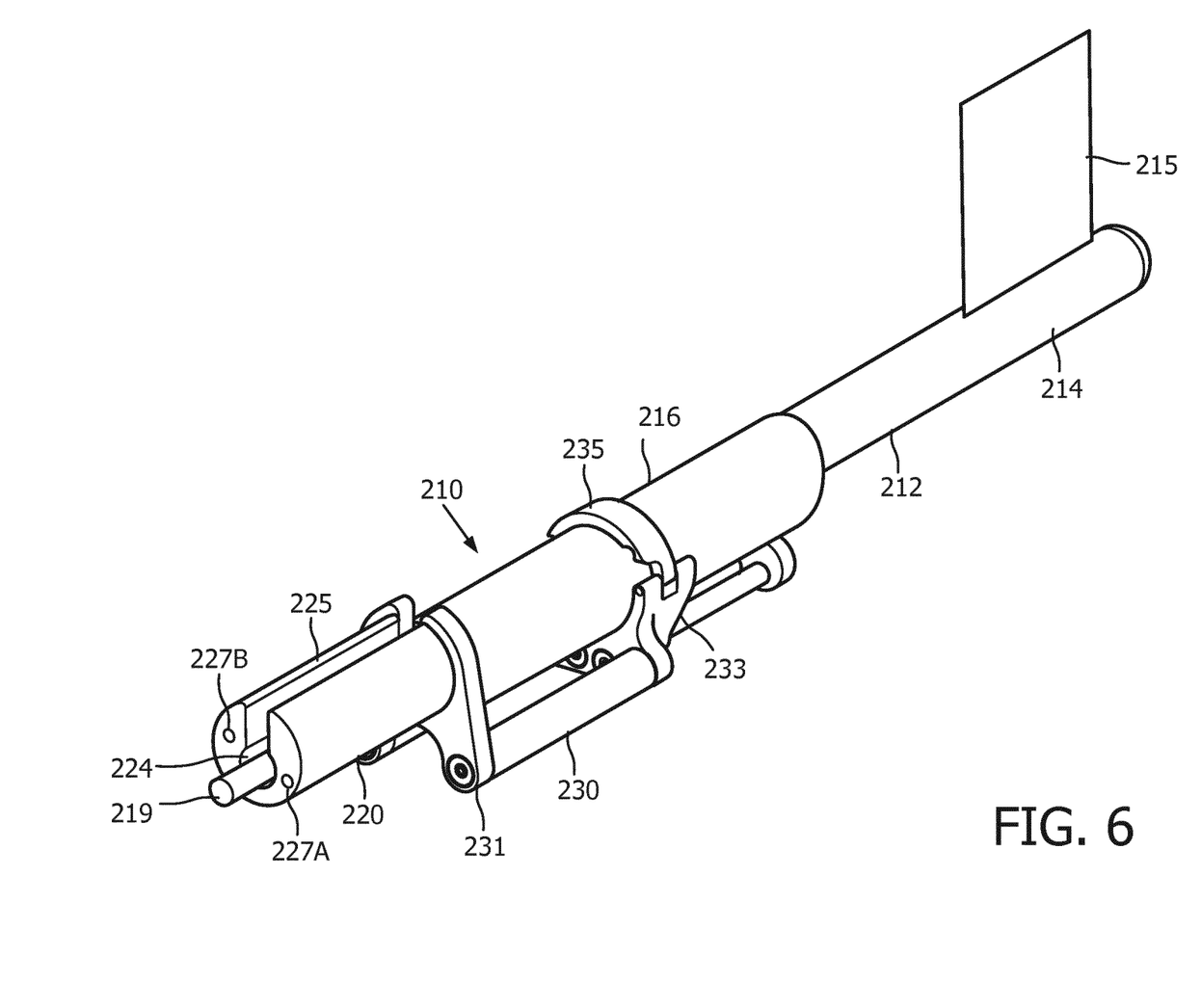
FIG. 6 is a perspective view of the ultrasound probe and the probe mounting structure attached to the rotating shaft for use in the transperineal stepper, according to a representative embodiment.

FIG. 6 is a perspective view of the ultrasound probe and the probe mounting structure attached to the rotating shaft of FIGS. 3A and 3B for use in the transperineal stepper, according to a representative embodiment. Notably, FIG. 6 additionally shows the shaft groove 225 in the shaft 220 for accommodating insertion of the cable 219.

Referring to FIG. 6, the ultrasound probe 210 is attached to the probe mounting structure 230, which is attached to the shaft 220. The ultrasound probe 210 includes the elongated neck 212 and the elongated body 216 arranged end-to-end, and the at least one ultrasound transducer 214 (e.g., ultrasound transducer array) positioned at the distal end of the elongated neck 212 for providing the image field 215. The elongated body 216 is secured to the support 233 of the probe mounting structure 230 by the clamp 235. The probe mounting structure 230 is secured or fixed to the shaft 220 via the flange 231. The shaft 220 defines the shaft channel 224 and the shaft groove 225, where the shaft groove 225 exposes the shaft channel 224, enabling insertion (via the shaft groove 225) of the cable 219 into the shaft channel 224 and the internal channel 211 of the ultrasound probe 210. The cable 219 and/or wiring extending from the cable 219 runs within the internal channel 211 to the ultrasound transducer 214, providing electrical power and/or electrical signaling connections.

Figure 7:
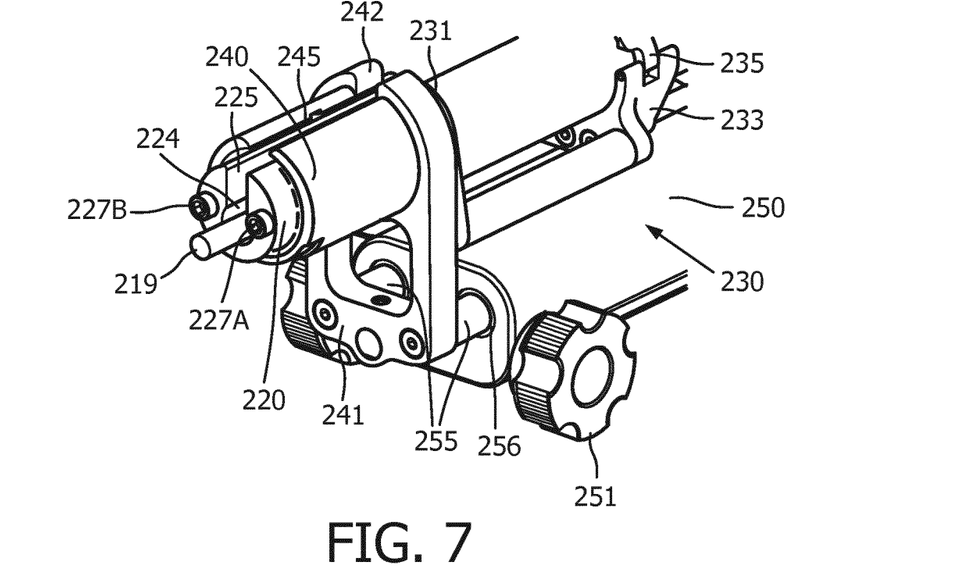
FIG. 7 is a perspective view of a shaft housing of the rotating shaft for use in the transperineal stepper, according to a representative embodiment.

FIG. 7 is a perspective view of a rotating shaft and a shaft housing for use in the transperineal stepper, according to a representative embodiment.

Referring to FIG. 7, a shaft housing 240 is configured to contain the shaft 220. The shaft housing 240 defines a longitudinal housing groove 245 that is alignable with the longitudinal shaft groove 225 in the shaft 220 to enable placement of the at least one cable 219 within the shaft channel 224. The shaft housing 240 is held in place by a housing frame 241, which in the depicted embodiment, is connected to a longitudinal translation device comprising rods 255 configured to slide through corresponding longitudinal bores 256 in a base 250 of the transperineal stepper, for example, through manual operation of rotating knob 251. (Another rotating knob 251 (not shown) may be arranged on the opposite side of the base 250.) Accordingly, longitudinal motion or sliding of the rods 255 through the corresponding bores 256 of the base 250 results in movement, as a unit, of the housing frame 241 and housing 240. This, in turn, results in corresponding longitudinal movement, as a unit with the housing frame 241 and the housing 240, of the shaft 220, the probe mounting structure 230 attached to the shaft 220 via the flange 231, and the ultrasound probe 210 attached to the probe mounting structure 230 to a desired position. For example, the longitudinal movement of the ultrasound probe 210 causes movement of the elongated neck 212 within the patient for ultrasound imaging. The shaft 220 is rotatable within the otherwise fixed shaft housing 240, resulting in corresponding rotation of the probe mounting structure 230 and the ultrasound probe 210 attached to the probe mounting structure 230, as discussed above. This results in angular positioning of the ultrasound transducer 214 within the patient to obtain the desired ultrasound imaging.

Figure 8A:
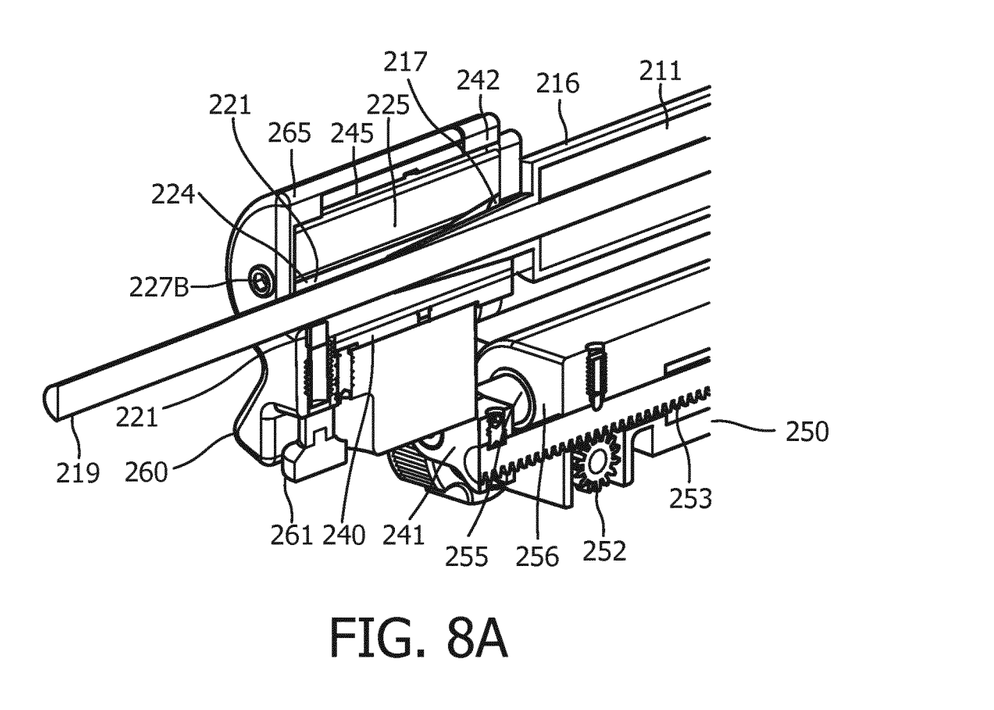
FIG. 8A is a cross-section view of a rotating handle for operating the rotating shaft within the shaft housing shown in FIG. 7 for use in the transperineal stepper, according to a representative embodiment.
Figure 8B:
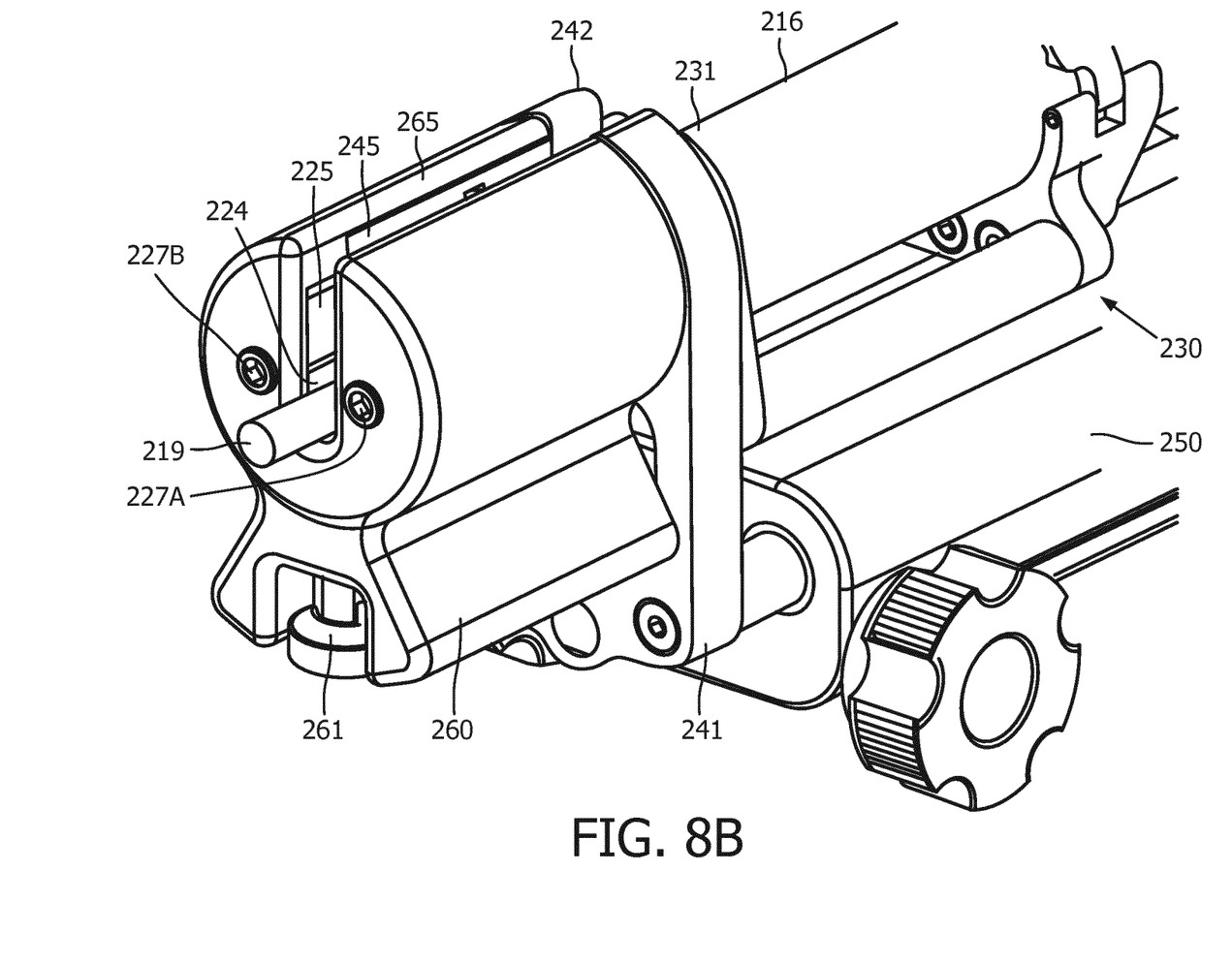
FIG. 8B is a perspective view of rotating handle in FIG. 8A for operating the rotating shaft for use in the transperineal stepper, according to a representative embodiment.

FIG. 8A is a cross-section view of a rotating handle for operating the rotating shaft within the shaft housing shown in FIG. 7 for use in the transperineal stepper, and FIG. 8B is a perspective view of rotating handle in FIG. 8A for operating the rotating shaft for use in the transperineal stepper, according to a representative embodiment.

Referring to FIGS. 8A and 8B, an example implementation is depicted in which the rod(s) 255 are caused to slide through the bores 256. In particular, the rotating knob 251 is connected to a gear 252 having teeth adapted to enmesh with teeth of a rail 253 within the base 250. As the gear 252 rotates clockwise (in response to movement of the rotating knob 251), longitudinal movement toward the distal end of the base 250 is translated to the rail 253, causing the ultrasound probe 210 to move toward or into the patient. As the gear 252 rotates counterclockwise, longitudinal movement toward the proximal end of the base 250 is translated to the rail 253, causing the ultrasound probe 210 to move away from or out of the patient. Of course, other mechanisms located in the base 250 or otherwise, may be incorporated to enable longitudinal movement of the assembly including the shaft 220, the probe mounting structure 230 and the ultrasound probe 210, without departing from the scope of the present teachings.

Also, as shown in FIG. 8A, the shaft 220 includes the shaft channel 224, which contains the strain relief 217 and the cable 219. The shaft groove 225 of the shaft 220, which in the depicted neutral position of the shaft 220, is aligned with the housing groove 245 of the housing 240, a handle groove 265 of handle 260 (discussed below), as well as a housing frame groove 242 in the housing frame 241. This alignment enables insertion of the cable 219 through the aligned handle groove 265, housing groove 245 and shaft groove 225 into the shaft channel 224. Then, when the shaft 220 is rotated to various positions within the shaft housing 240, the shaft groove 225 may no longer be aligned with the housing groove 245 (and the frame groove 242). However, once the cable 219 is within the shaft channel 224, alignment of the shaft groove 225 with the housing groove 245 and the housing frame groove 242 is no longer necessary, enabling ease of cable management during manipulation of the transperineal stepper. The shaft 220 also includes the shaft pins 227A and 227B projecting from the proximal end of the shaft 220, as well as the hole 221 in the bottom portion of the shaft 220, enabling attachment of the shaft 220 to the handle 260 via a screw 261.

FIG. 8B is a perspective view of the rotating handle 260 for use in the transperineal stepper, mentioned above, according to a representative embodiment. Referring to FIG. 8B, the handle 260 surrounds both the shaft housing 240 and the shaft 220. In the depicted example, the handle 260 is physically connected to the shaft 220 by the shaft pins 227A and 227B extending through corresponding holes 267A and 267B through the proximal end of the handle 260. The handle 260 is further connected to the shaft 220 by the screw 261 extending through the hole 221 of the shaft 220. Of course, other means of physically connecting the handle 260 the shaft 220 may be incorporated without departing from the scope of the present teachings. The handle 260 prevents the shaft 220 from sliding longitudinally within the shaft housing 240. Rotation of the handle 260 causes corresponding rotation of the shaft 220 around the third longitudinal axis 220', which further causes rotation of the elongated neck 212 around the first longitudinal axis 212'.

The handle 260 defines the longitudinal handle groove 265, mentioned above, that is alignable with the housing groove 245 and the frame groove 242, and is aligned with the shaft groove 225, enabling placement of the at least one cable 219 in the shaft channel 224. Then, when the shaft 220 is rotated to various positions by operation of the handle 260 within the shaft housing 240, the shaft groove 225 and the handle groove 265 (which rotate together) may no longer be aligned with the housing groove 245 (and the frame groove 242). In other words, the handle 260 defines a longitudinal handle groove 265 that is in a fixed alignment with the longitudinal shaft groove 225 throughout rotational operation of the ultrasound probe 210, and is aligned with the longitudinal housing groove 245 (and the housing frame groove 242) in a neutral position of the shaft 220. However, once the cable 219 is within the shaft channel 224, alignment of the shaft groove 225 and the handle groove 265 with the housing groove 245 and the housing frame groove 242 is no longer necessary, enabling ease of cable management during manipulation of the transperineal stepper. Of course, means of rotating the shaft 220 and/or preventing the shaft 220 from sliding longitudinally within the housing 240 may be incorporated without departing from the scope of the present teachings.

Figure 9:
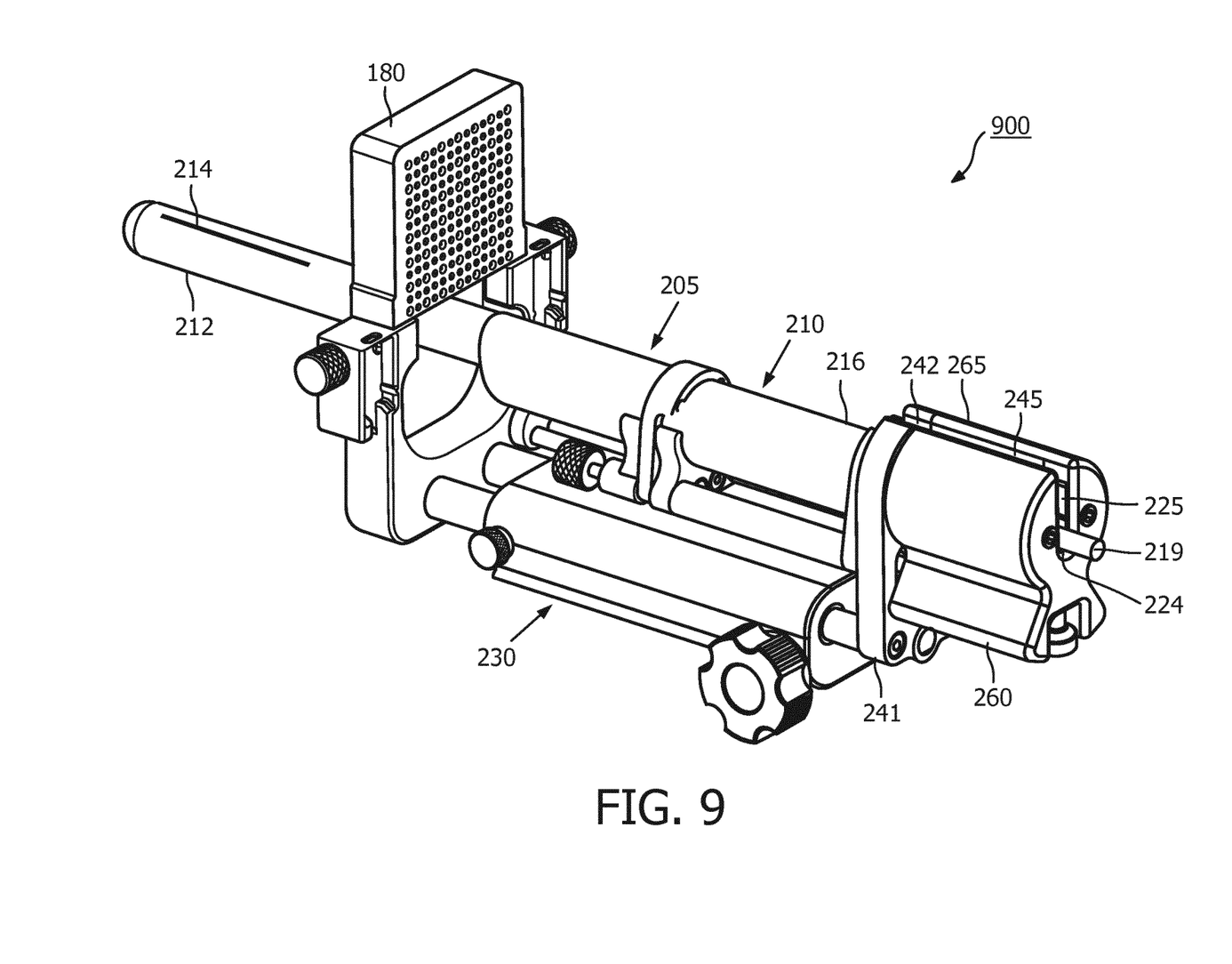
FIG. 9 is a perspective view of a transperineal stepper system including a transperineal stepper with a rotating shaft and an attached grid plate, according to a representative embodiment.

FIG. 9 is a perspective view of a transperineal stepper system including a transperineal stepper with a rotating shaft and an attached grid plate, according to a representative embodiment.

Referring to FIG. 9, transperineal stepper system 900 includes a transperineal stepper 205, having the ultrasound probe 210 positioned in the probe mounting structure 230, and a grid plate 180. The ultrasound probe 210 includes the elongated neck 212, at least one ultrasound transducer 214 connected to a distal end of the elongated neck 212, and an elongated body 216 connected to a proximal end of the elongated neck 212. The grid plate 180 is shown to include an array of grid holes, e.g., which are needle guides through which a needle can be placed. The transperineal stepper 205 further includes the shaft 220, which defines the shaft channel 224 and the shaft groove 225 (for accessing the shaft channel 224). The cable 219 of the ultrasound probe is placed in the shaft channel 224 through the shaft groove 225, enabling easy cable management during operation of the transperineal stepper system 900.

The transperineal stepper 205 further includes the handle 260, which encompasses the shaft housing 240 and the shaft 220. Rotation of the handle 260 causes corresponding rotation of the shaft 220, and thus rotation of the elongated neck 212 of the ultrasound probe 210, as discussed above. The handle 260 also prevents the shaft 220 from sliding longitudinally within the shaft housing 240. The handle 260 defines a longitudinal handle groove 265 that is alignable with the housing groove 245 and the frame groove 242, and is aligned with the shaft groove 225 of the shaft 220, enabling placement of the at least one cable 219 in the shaft channel 224, when all the grooves are in alignment. When the shaft 220 is rotated to various positions by operation of the handle 260 within the shaft housing 240, the shaft groove 225 and the handle groove 265 rotate together, while the cable 219 remains within the shaft channel 224, enabling ease of cable management during manipulation of the transperineal stepper 205.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

According to an aspect of the present disclosure, a device is provided that includes an ultrasound probe, a shaft and at least one cable. The ultrasound probe includes an elongated neck insertable in a patient and rotatable around a first longitudinal axis, where at least one ultrasound transducer is connected to a distal end of the elongated neck, and an elongated body connected to a proximal end of the elongated neck and rotatable around a second longitudinal axis that is parallel to and offset from the first longitudinal axis, where the elongated body is removably attached to a probe mounting structure. The shaft is arranged at a proximal end of the elongated body and attached to a proximal end of the probe mounting structure, where rotation of the shaft causes corresponding rotation of the probe mounting structure and the attached elongated body of the ultrasound probe around the second longitudinal axis to a desired position. The shaft defines a longitudinal shaft channel in an interior portion of the shaft and a longitudinal shaft groove extending from a surface of the shaft to the longitudinal shaft channel. The at least one cable provides electrical connections to the at least one ultrasound transducer, where the at least one cable is insertable into the longitudinal shaft channel through the longitudinal shaft groove, and enters an internal channel of the ultrasound probe through the longitudinal shaft channel to enable electrical connection with the at least one ultrasound transducer.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A device, comprising:
   an ultrasound probe comprising:
      an elongated neck insertable in a patient and rotatable around a first longitudinal axis that is centrally disposed within the elongated neck, wherein at least one ultrasound transducer is connected to a distal end of the elongated neck; and
      an elongated body connected to a proximal end of the elongated neck and rotatable around a second longitudinal axis that is centrally disposed within the elongated body and parallel to and offset from the first longitudinal axis, wherein the elongated body is removably attached to a probe mounting structure;

a shaft arranged at a proximal end of the elongated body and attached to a proximal end of the probe mounting structure, the first longitudinal axis extending through the shaft and the elongated body, the rotation of the shaft about the first longitudinal axis causing corresponding rotation of the probe mounting structure and the attached elongated body of the ultrasound probe around the second longitudinal axis to a desired position, wherein the shaft defines a longitudinal shaft channel in an interior portion of the shaft and a longitudinal shaft groove extending from a surface of the shaft to the longitudinal shaft channel; and at least one cable for providing electrical connections to the at least one ultrasound transducer, wherein the at least one cable is insertable into the longitudinal shaft channel through the longitudinal shaft groove, and enters an internal channel of the ultrasound probe through the longitudinal shaft channel to enable electrical connection with the at least one ultrasound transducer.

2. The device of claim 1, wherein the at least one ultrasound transducer comprises an ultrasound transducer array.

3. The device of claim 1, wherein the shaft is a rotatable around a third longitudinal axis that is parallel to and longitudinally aligned with the first longitudinal axis of the elongated neck.

4. The device of claim 3, further comprising:

a shaft housing containing the shaft, the shaft being rotatable around the third longitudinal axis within the shaft housing, wherein the shaft housing defines a longitudinal housing groove that is alignable with the longitudinal shaft groove in the shaft to enable placement of the at least one cable within the longitudinal shaft groove.

5. The device of claim 4, further comprising:

a handle containing the shaft housing and connected to the shaft within the shaft housing, preventing the shaft from sliding, rotation of the handle causing corresponding rotation of the shaft around the third longitudinal axis of the shaft, wherein the handle defines a longitudinal handle groove alignable with the longitudinal housing groove and aligned with the longitudinal shaft groove, enabling placement of the at least one cable in the longitudinal shaft groove.

6. The device of claim 1, wherein the probe mounting structure comprises a support configured to receive the elongated body of the ultrasound probe, and a clamp configured to mechanically secure the elongated body in the support, such that the elongated body is in a fixed position relative to the probe mounting structure.

7. The device of claim 6, wherein the probe mounting structure further comprises a flange at the proximal end of the probe mounting structure, the shaft being attached to the flange.

8. The device of claim 7, further comprising:

a base connected between the shaft housing and a grid plate comprising an array of grid holes, wherein at least one needle is guided through at least one hole of the array of grid holes.

9. The device of claim 8, wherein the base comprises:

a longitudinal translation device arranged between the shaft housing and the grid plate, enabling movement, as a unit, of the shaft housing, the shaft contained in the shaft housing, the probe mounting structure attached to the shaft, and the elongated body of the ultrasound probe secured to the probe mounting structure toward and away from the grid plate, the longitudinal translation device comprising:

at least one longitudinal bore in the base; and at least one rod attached to the shaft housing at a proximal end of the at least one rod, and configured to move longitudinally through the at least one longitudinal bore in the base.

* * * * *